United States Patent [19]
Morris

[11] Patent Number: 5,562,659
[45] Date of Patent: Oct. 8, 1996

[54] ELECTRO-SURGICAL INSTRUMENT AND METHOD OF FABRICATION

[75] Inventor: James R. Morris, Evergreen, Colo.

[73] Assignee: Materials Conversion Corp., Wheeling, Ill.

[21] Appl. No.: 943,223

[22] Filed: Sep. 9, 1992

[51] Int. Cl.$^6$ ................................................ A61B 17/39
[52] U.S. Cl. ........................... 606/41; 606/45; 606/46; 128/642
[58] Field of Search ........................ 606/27–34, 37–42, 606/45–52; 128/642

[56] References Cited

U.S. PATENT DOCUMENTS

| | | | |
|---|---|---|---|
| 4,145,764 | 3/1979 | Suzuki et al. | 427/2 X |
| 4,228,800 | 10/1980 | Degler, Jr. et al. | 606/50 X |
| 4,726,368 | 2/1988 | Morris | 606/151 |
| 4,850,353 | 7/1989 | Stasz et al. | 606/45 X |
| 4,869,248 | 9/1989 | Narula | 606/45 |
| 4,960,419 | 10/1990 | Rosenberg | 606/45 |
| 5,026,370 | 6/1991 | Lottick | 606/45 X |
| 5,221,281 | 6/1993 | Klicek | 606/45 |

OTHER PUBLICATIONS

Peters, J. H. et al., Safety and efficacy of laperoscopic cholecystectomy . . . , *Ann. Surg.*, Jan. 1991.
Wicker, P., The hazards of electrosurgery and principles of safe use, Natnews, Nov. 1990.
Association of Operating Room Nurses, Proposed recommended practices: Electrosurgery, AORN Journal, Aug. 1990.

*Primary Examiner*—Angela D. Sykes
*Assistant Examiner*—M. Peffley
*Attorney, Agent, or Firm*—Olson & Hierl, Ltd.

[57] ABSTRACT

A method for producing an exceptionally durable electrical insulation coating for electro-surgical instrumentation with excellent insulative properties in the 500 KHZ to 1 MHZ frequency range which can drastically reduce, if not totally eliminate, many problems of current electrical insulation materials in use. A process of ceramic plasma deposition is used. A thin ceramic coating can be readily applied to new or existing mono/bipolar surgical instrumentation.

5 Claims, 2 Drawing Sheets

ELECTRO-SURGICAL INSTRUMENT AND METHOD OF FABRICATION

This invention relates to electro-surgical instruments and apparatus and more particularly with to electro-surgical instruments with ceramic deposited insulative coating.

U.S. PATENTS OF POSSIBLE RELEVANCE

| | | |
|---|---|---|
| 2,865,375 | 12/1958 | Banks et al. |
| 2,865,275 | 12/1958 | Pellier & DiPielro |
| 2,975,078 | 03/1961 | Rayfield |
| 3,210,220 | 10/1965 | Clegg & Greening |
| 3,480,483 | 11/1969 | Wilkinson |
| 3,721,534 | 03/1973 | Kubick |
| 3,892,883 | 06/1975 | Leclercq |
| 4,314,005 | 02/1982 | Arias |
| 4,483,899 | 11/1984 | Kuwabara |
| 4,497,877 | 02/1985 | Krijl & Van de Leest |
| 4,518,467 | 05/1985 | Mason et al. |
| 4,726,368 | 02/1988 | Morriss |

ADDITIONAL REFERENCES

1. Peters, J. H., et al. Safety and efficacy of laparoscopic cholecystectomy. A prospective analysis of 100 initial patients. Annual Surgery, Jan., 1991.
2. Wicker, P. The hazards of electrosurgery and principles of safe use. NATNEWS, Nov. 1990.
3. Association of Operating Room Nurses. Proposed recommended practices: Electrosurgery. AORN Journal, Aug., 1990.

DISCUSSION OF U.S. PATENTS

U.S. Pat. No. 2,865,375 relates to corrosion-resistant needles plated with a shiny, corrosion-resistant, flexible nickel-nickel/phosphate plate, while U.S. Pat. No. 2,865,376 relates to a process for preparing shiny, corrosion-resistant gold plated needles for surgical sutures.

U.S. Pat. No. 2,975,078 teaches a method for preparing ceramic coated wire suitable for electric instrumentation which is subjected to very high temperatures and consisting of a nickel oxide surface coated with a ceramic composition comprising 6 to 9 different oxides and dioxides including lead, titanium, silicon, magnesium, baron and 1 to 4 additional oxides and/or dioxides.

U.S. Pat. No. 3,005,729 relates to a surface blackening process for steels, while U.S. Pat. No. 3,210,220 relates to a process limited to coating stainless steel comprising a tightly adhering oxide film produced by subjecting a steel-chromium alloy surface of an object to the action of a concentrated sulfuric or nitric acid water solution of chromium trioxide, $CrO_3$, for a length of time necessary to form the desired thin oxide coating.

U.S. Pat. No. 3,480,483 relates to a process for forming a coating on the cutting edge of steel razor blades by applying a thin layer of chromium to the surface and heat treating in an oxidizing atmosphere, thus giving enhanced durability to the cutting edge.

U.S. Pat. No. 3,721,534 relates to casting aluminum articles consisting of a ferrous metal substrate with three layer coating suitable for casting molten aluminum, with the coating able to withstand the temperature of molten aluminum, being insoluble in molten aluminum, having good heat transfer and allows separation of a smooth cast aluminum article and consisting of nickel aluminide, nickel-chromium alloy and aluminum oxide ceramic.

U.S. Pat. No. 3,892,883 is a process for improving cohesion using copper/glass, nickel aluminide and finally a metal oxide of carbide.

U.S. Pat. No. 4,314,005 relates to a process for thermo-chemically coating ferrous metal articles. This involves the following process, namely, preparing a coating composition for homogenizing a complex of metal oxides and other solids in an organic liquid composition to obtain an emulsion, preheating the ferrous articles to an elevated temperature, followed by coating the preheated articles.

U.S. Pat. No. 4,483,899, related to an infrared reflection-preventing film which includes a titanium oxide layer disposed on an infrared optical substrate, is taught U.S. Pat. No. 4,483,899.

U.S. Pat. No. 4,497,877 relates to a method to protect a metal article against corrosion and scratching comprising first plating with a nickel-phosphorous alloy and secondly, a coating comprising $CrPO_4$, $Cr(OH)_3$ and, optionally, $Cr2(SO_4)_3$ but no nickel, while U.S. Pat. No. 4,497,877 relates to a metal article which is coated with a protective layer comprising $CrPO_4$, $Cr(OH)_3$ and may also comprise $Cr2(SO_4)_3$ but in which no nickel is present. This layer provides corrosion protection.

U.S. Pat. No. 4,518,467 relates to a process for the production of a solar collector for high temperature using a porous oxide film on a stainless steel surface, and U.S. Pat. No. 4,726,368 describes a non-reflective instrument and in particular, the invention relates to non-reflective surgical instruments for use in laser surgery, comprising a metallic substrate and a coating selected from the group consisting of $Al_2O_3$, $Al_2O_3/TiO$ mixtures, $Al_2O/Cr_3O_2$ mixtures and WC/Co mixtures. This coating is a non-reflective material which absorbs radiation in the infrared region.

Each of the patents and other references discussed on pp. 1–4 is hereby specifically incorporated by reference for all that is disclose therein.

BACKGROUND OF THE INVENTION

Since the inception of the monopolar and bipolar electro-surgical unit in surgery as tools to the surgeon for cutting and coagulating tissues, numerous cases of inadvertent and unwanted electrical shocks and burns to the patient and physician have been reported (Peters, 1991; Wicker, 1990; Association of Operating Room Nurses, 1990). In a great number of these reports, the cause of the reported injury was specified as resulting from the breakdown of the electro-surgical instrument's insulation.

The insulation material typically utilized has been teflon, PVC, or heat shrink plastic materials. While these materials do have exceptionally well-documented electrical insulative characteristics, they are severely lacking as ideal insulators for surgical instruments. The primary reasons for this are that they have very little abrasion resistance (i.e. coating wears off easily). In addition, they can be scratched easily, leaving areas with bare metal exposed. They degrade rapidly with various sterilization methods, causing insulative properties to deteriorate; and additionally, they can retain moisture between bare metal and insulation contributing to problems of corrosion and to problems with sterilization.

Also they have low resistance to heat. The insulation degrades with heat generated by wattage flowing through the instrument during prolonged use, and finally the currently utilized instrument insulations must be replaced regularly which results in excessive costs to health care providers.

It is the applicant's belief after analysis of the technology that the ideal insulator for electro-surgical instruments would have at least the following characteristics. It should have excellent dielectric (insulative) properties in the 500 KHZ to 1 MHZ frequency range which is typical of electrosurgery unit generators. In addition, it should have exceptional wear and abrasion characteristics, and should be impervious to scratching, nicking or cutting. It should be chemically inert and sterilizable, non-toxic, non-irritating, and non-cytotoxic, and be acceptable for use in the human body. It should adhere rigidly to the base metal of the instrument to prevent corrosion and sterility problems. It should be cost effective and it should be unaffected by various sterilization techniques and finally it should be readily applicable to a variety of shapes and sizes of surgical instruments.

SUMMARY AND OBJECTS OF THE INVENTION

Through utilization of a plasma gun, detonation gun or high velocity oxygen feed (HVOF) system for ceramic deposition coating, the above itemized ideal characteristics have been achieved. The particular ceramic of choice is $Al_2O_3$ (aluminum oxide) although magnesium oxide/zirconia yttria/zirconia-calcia coating could also be utilized. The $Al_2O_3$ material has an inherently greater dielectric strength and therefore allows thinner coating to achieve the same insulative capacity as the other commonly used materials when applied in thicker coating.

The preferred thickness of the coating for most surgical instrument applications has been found to be 0.010 to 0.015 inches. Coatings in this thickness range have been tested and found to be excellent insulators up to at least 4–6 kilovolts, 3,000–4,000 volts, alternating current RMS.

DC current leakage at 3,000 volts has been tested and found to be less than 100 micro amps.

Coatings of $Al_2O_3$ have been tested and found to be non-toxic, non-cytotoxic, and non-irritating.

The preferred coating has also been found not to degrade through repeated sterilization methods of chemical soak, steam and autoclave sterilization.

This coating has also been wear and abrasion tested by placing coated samples in a rock tumbler device for 24 hours. This is roughly equivalent to 3–4 hours on a grinding wheel. The results of this test indicated that less than 1/1000 of an inch of coating material was removed.

Further tests designed to indicate the coating's resistance to scratching and nicking have been performed through purposeful and continual scratching and cutting of the coating with stainless steel scalpel blades and scissor blades. Because the $Al_2O_3$ coating is so much harder than the typical stainless steel, no cuts or scratches were obtained. Instead, the metal of the stainless steel blades was worn off by the coating.

The characteristics of this coating should lead to significant cost savings to users through eliminating the additional expenses of replacing typical teflon and plastic based insulation materials.

In addition, due to the combination of characteristics described, a significantly safer instrument is produced and hospital and physician risk are decreased.

OBJECTS OF THE INVENTION

One object of this invention is to provide an insulative coating for electro-surgical instruments which has exceptional wear and abrasion characteristics and is impervious to scratching, nicking and cutting.

A further object of this invention is to provide an insulative coating for electro-surgical instruments which has excellent dielectric (insulative) properties in the 500 KHZ to 1 MHZ frequency range.

An additional object of this invention is to provide an insulative coating for electro-surgical instruments which is chemically inert and sterilizable, non-toxic, non-irritating, and non-cytotoxic.

It is another object of this invention is to provide an insulative coating for electro-surgical instruments which adheres rigidly to the base metal of the instrument to prevent corrosion and sterility problems.

And a further object of this invention is to provide an insulative coating for electro-surgical instruments which is unaffected by various sterilization techniques.

It is also an object of this invention to provide an insulative coating for electro-surgical instruments which is readily applicable to a variety of shapes and sizes of surgical instruments.

DESCRIPTION OF PREFERRED EMBODIMENTS

Figure 1:
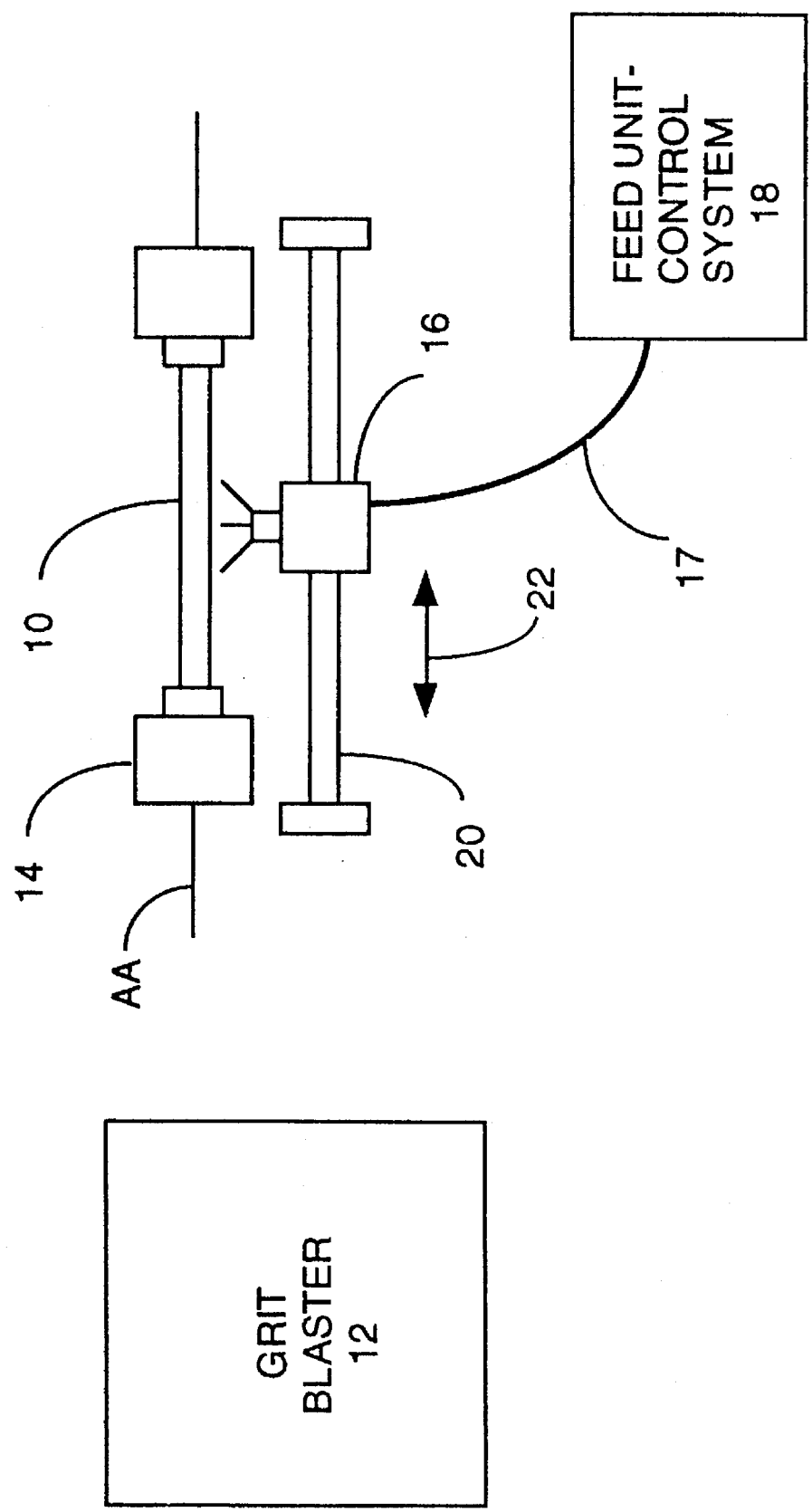
FIG. 1 is a schematic illustration of apparatus for applying an electrical insulation coating to an electro-surgical instrument.

FIG. 1 illustrates a method for providing an insulation coating on an electro-surgical instrument 10, such as a reusable endoscopic electrode having a length of 16 in. and a diameter of 0.065 in. which is constructed from surgical stainless steel. Initially the instrument is masked to cover areas thereon which are not to be coated. The masking may be performed manually using conventional masking tape.

The instrument is next placed in a conventional grit blaster 12, such as for example that sold under the product designation Trinco Dry Blast Sand Blaster 36-BP2 which is commercially available from Trinity Tool Company 34600 Commerce Road, Fraser, Minn., 48026. The surface of the instrument is cleaned and slightly roughened by the grit blaster.

The instrument is next mounted on a spindle assembly 14 with the longitudinal axis of the instrument coaxially aligned with the axis of rotation AA of the spindle assembly 14.

A coating applicator system which may comprise a plasma gun 16 connected by feed conduit 17 to material feed and control unit 18 is provided for spraying coating material in a plasma state onto the surface of the instrument. The coating applicator system may be an applicator system of a conventional type well known in the art such as for example that sold under the product designation Plasmatron® Thermal Spray System Model #3700-$B_2$B-100-D which is commercially available from Miller Thermal, Inc. Plasmadyne and Mogul Products, 555 Communication Dr., P.O. Box 1081, Appleton, Wis. 54912. Coating material which is to be applied to an instrument 10 is initially placed in the material feed unit 18 in a powdered form. Powdered forms of the materials which may be used in the coating process, including aluminum oxide, an aluminum oxide and titanium dioxide mixture, and molybdenum are commercially available under the product designations AI-1010 F, AI-1070, and AI-1138, respectively, from Alloys International Products, 1901 Ellis School Road, Baytown, Tex. 77521.

Figure 2:
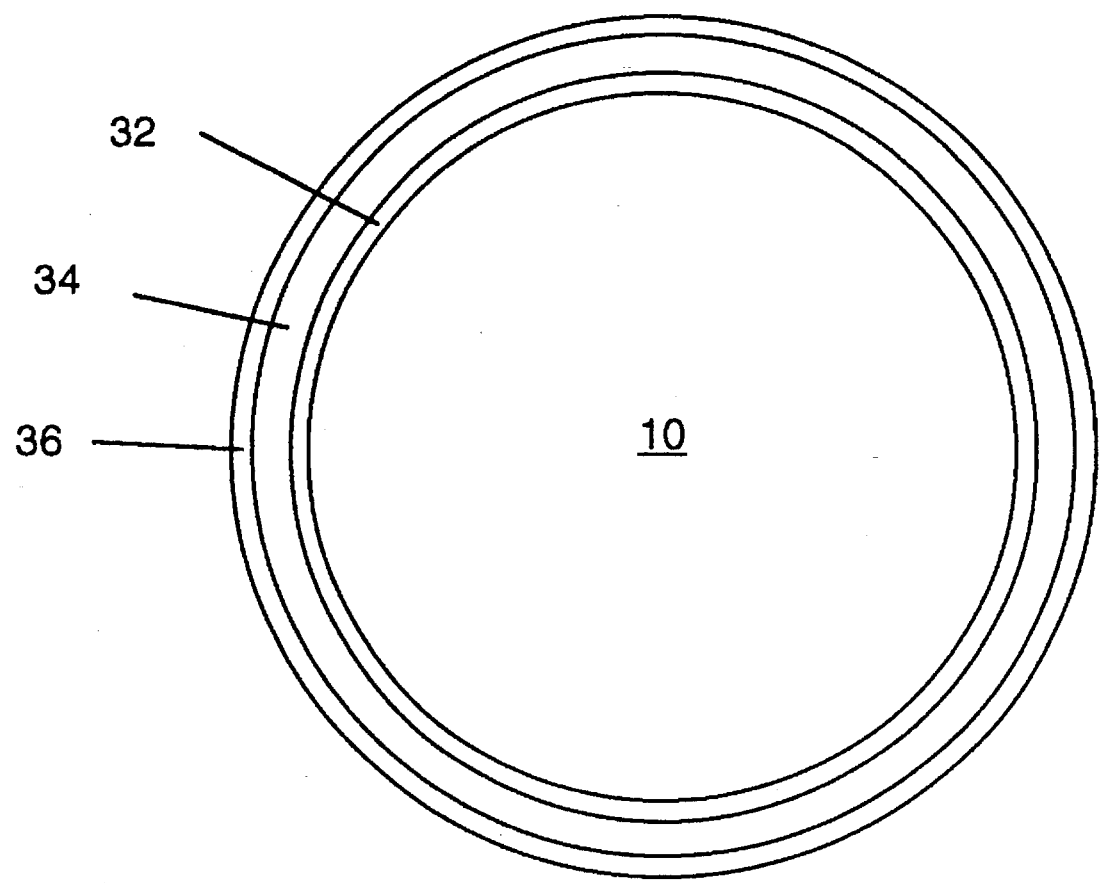
FIG. 2 is a cross sectional view of an electro-surgical instrument with an insulation coating.

The spindle assembly 14 is positioned with its axis of rotation AA parallel to a guide assembly 20 which is adapted to support plasma gun 16 thereon for reciprocal motion 22. The tip of the gun 16 may be positioned 3.5 in. for the surface of the instrument 10. In a typical application the gun may be reciprocated back and forth at an average speed of approximately 1 ft./sec. and the instrument may be rotated by the spindle about axis AA at a rate of approximately 250 revolutions per minute. Cooling air may be applied to the instrument as from adjacent air jet nozzles (not shown) to cool the coating material after it is applied to the instrument. Although coated instrument having the wear and insulating properties described elsewhere herein may be obtained through direct application of a single coating layer, such as a layer of aluminum oxide, to the instrument, in a preferred embodiment of the invention three separate coatings are applied to the instrument: a bonding layer 32 (which may be molybdenum-powder #AI-1138 having a thickness of 0.001 in.), an insulative protection layer 34 (which may be aluminum oxide-powder #AI-1010 F having a thickness of 0.020 in.), and a color (black) layer 36 (which may be aluminum oxide and titanium dioxide-powder #AI-1070 having a thickness of 0.001 in.), FIG. 2. The bonding layer 32 improves the bonding of the insulative layer 34 to the instrument. The color layer may be applied to reduce glare from the instrument when it is used in a surgical procedure. After the ceramic coatings have been applied, a moisture barrier sealing layer may be applied to the instrument. One manner of applying a sealing layer is to hand-rub the instrument with silicone sealant and then heat the instrument with four 175-Watt lamps for about 30 minutes. Thereafter, excess sealant is removed by scrubbing and wiping the instrument with acetone.

Specific production parameters for the different powders listed above for use with the equipment described above are provided in the Appendix which is hereby incorporated by reference and which forms a part of the disclosure of this patent application for all that is set forth therein. In addition to the above-described plasma gun coating procedures, other coating procedures known in the ceramic arts such as detonation guns and high-velocity oxygen feed systems could also be used. A plasma gun is currently the best mode contemplated for applying a coating. When nonuniform articles are to be coated, the article may be held manually as with tongs and manually rotated and reciprocated in front of a ceramic applicator gun. Instruments coated with ceramic in the manner described above were tested and evaluated as described below. The same procedure as described above may be used to apply a coating of magnesium oxide, zirconia yttria, or zirconia-calcia rather than aluminum oxide to form an insulative coating.

The durability is first evaluated. Samples of a ceramic composite coating are processed in a rock tumbler device for 25 hours. This amount of wear is roughly equivalent to the wear which would be produced by 3–4 hours on a grinding wheel. The ceramic coating was not chipped or cracked after this treatment. From visual analysis under high magnification, it can be estimated that less than 1/1000 of an inch of coating material is removed during the experiment.

The toxicology is next studied. The results of toxicological evaluation of coated stainless steel samples are shown in Table 1.

TABLE 1

| Toxicology Results | |
|---|---|
| Percent inhibition of cell growth QCOP L300 | Non-inhibitory |
| Medium eluate method QCOP L305 | Non-cytotoxic |
| Agar overlay QCOP L303 | Non-cytotoxic |
| USP intracutaneous irritation QCOP B309 | |
| Normal saline extract | Non-irritating |
| Cottonseed oil extract | Non-irritating |
| USP mouse systemic injection QCOP B305 | |
| Normal saline extract | Non-toxic |
| Cottonseed oil extract | Non-toxic |
| Rabbit subcutaneous implantation | Non-irritating |

Electrical insulative properties are next considered. Table 2 illustrates the properties of the electrical insulative coating.

TABLE 2

| Physical properties of the electrical insulative coating | |
|---|---|
| Application | Two coat plasma deposition |
| Insulative capacity | Greater that 3,000 v/mm |
| MOHS Hardness Scale (Diamond hardness = 10.0) | 9.2 |
| Tensile bond strength (psi) | >8,000 |
| Modulus of rupture (psi) | 19,000 |
| Modulus of elasticity ($10^6$ psi) | 11 |
| Density (G/cm3) | 3.6 |
| Metallographic Porosity (volume %) | <1 |
| Surface Finish As-coated (Microinch rms) | 150 |

While illustrative and presently preferred embodiments of the invention have been described in detail herein, it is to be understood that the inventive concepts may be otherwise variously embodied and employed and that the appended claims are intended to be construed to include such variations except insofar as limited by the prior art.

APPENDIX A

| OPERATING MODE | Parameters for Plasmatron ® Thermal Spray System | | |
|---|---|---|---|
| | POWDER NO. AI-1010F SUB-SONIC 40 KW | POWDER NO. AI-1138 SUB-SONIC 40 KW | POWDER NO. AI-1070 SUB-SONIC 40 KW |
| Spray Gun | SG-100 | SG-100 | SG-100 |
| Anode | 2083-155 | 355 | 155 |
| Cathode | 1083A-112 | 112 | 112 |
| Gas Injector | 2083-113 | 113 | 113 |
| Nozzle # | N/A | N/A | N/A |
| Operating Parameters Power | | | |
| Open Circuit Voltage | N/A | N/A | N/A |
| Operating Voltage | 34.6 | 42 | 40 |
| Operating Current | 900 | 800 | 800 |
| Arc Gas/Primary | Argon | Argon | Argon |
| Flow Rate | N/A | N/A | N/A |
| Critical Orifice No. | 56 | 56 | 56 |
| Press. Reg. $P_1$, psig | 50 | 50 | 50 |
| Auxiliary Gas/Secondary | Helium | Helium | Helium |
| FLow Rate | N/A | N/A | N/A |
| CriticaL Orifice No. | 80 | 80 | 80 |
| Press. Reg. $P_1$, psig | 100 | 100 | 100 |
| Powder Gas/Carrier | Argon | Argon | Argon |
| Flow Rate | N/A | N/A | N/A |
| Critical Orifice No. | 77 | 77 | 77 |
| Press. Reg. $P_1$, psig | 40 | 50 | 50 |
| Hopper Setting/RPM | 2.5 | 1.3 | 3.5 |
| Powder Port | N/A | N/A | N/A |
| Meter Wheel/RPM | 2.5 | 1.3 | 3.5 |
| Spray Distance | 3.5 in. | 3.5 in. | 3.5 in. |

What is claimed is:

1. An electro-surgical instrument comprising:
   (a) a surgical instrument substrate;
   (b) a durable ceramic coating on said substrate providing excellent electrical insulative properties to said substrate in the 500 KHZ to 1 MHZ frequency range and having a thickness of at least about 0.01 inches; and
   (c) a silicone sealant layer over said ceramic coating.

2. The electro-surgical instrument of claim 1, wherein said durable ceramic being selected from the group consisting of aluminum oxide, magnesium oxide, zirconia yttria and zirconia-calcia.

3. The electro-surgical instrument of claim 1, wherein the thickness of said ceramic composite coating is 0.010–0.03 inches.

4. The electro-surgical instrument of claim 1, wherein a molybdenum bonding layer is present between said substrate and said ceramic coating.

5. The electro-surgical instrument of claim 1, wherein a molybdenum bonding layer is present between said substrate and said ceramic coating and an aluminum oxide and titanium dioxide color layer is present over said ceramic coating.

* * * * *